United States Patent [19]

Bock et al.

[11] Patent Number: 5,556,947
[45] Date of Patent: Sep. 17, 1996

[54] MONOCLONAL ANTIBODY RECOGNIZING A SURFACE MOLECULE ON A SUBSET OF ANTIGEN-STIMULATED T CELLS AND ON CERTAIN MALIGNANCIES OF T AND B CELL ORIGIN

[75] Inventors: Glenn H. Bock; David L. Nelson, both of Bethesda; Carole C. Kurman, Potomac; Thomas A. Fleisher, Bethesda, all of Md.

[73] Assignee: The United States of America as represented by the Department of Health and Human Services, Washington, D.C.

[21] Appl. No.: 287,718

[22] Filed: Aug. 9, 1994

Related U.S. Application Data

[63] Continuation of Ser. No. 934,106, Aug. 21, 1992, abandoned.

[51] Int. Cl.$^6$ .................. A61K 39/395; C07K 16/18; C07K 16/28
[52] U.S. Cl. ................. 530/391.3; 530/388.2; 530/388.73; 530/388.75; 530/388.85; 530/391.7
[58] Field of Search ............... 530/387.1, 387.7, 530/388.1, 388.2, 388.7, 388.73, 388.75, 388.8, 388.85, 391.1, 391.3, 391.7; 435/70.21, 172.2, 240.27

[56] References Cited

FOREIGN PATENT DOCUMENTS

WO91/13632   9/1991   WIPO ................. A61K 39/00

OTHER PUBLICATIONS

Wu et al. Leukemia 4: 851–855 (1990).
K. Thielemans et al., "Strategies for Production of Monoclonal Anti–Idiotype Antibodies Against Human B Cells Lymphomas," *The Journal of Immunology,* 133(1):495–501 (Jul. 1984).
Van Snick, Jacques, "Interleukin–6: An Overview," *Annu. Rev. Immunol.* 8:253–78 (1900).
Kawano et al., "Autocrine Generation and Requirement of BSF–2/IL–6 for Human Multiple Myelomas," *Nature* 332:83–85 (1988).
Schwab et al., "Characterization of an Interleukin–6–Mediated Autocrine Growth Loop in the Human Multiple Myeloma Cell Line, U266," *Blood* 77:587–593 (1991).
Matsuda et al., "Establishment of an Interleukin 6 (IL6)/B Cell Stimulatory Factor 2–Dependent Cell Line and Preparation of Anti–IL 6 Monoclonal Antibodies," *Eur. J. Immunol.* 18:951–956 (1988).
Vitetta et al., "Memory B and T Cells," *Annu. Rev. Immunol.* 9:193–217 (1991).
Nishino et al., "Trophoblast–Derived Interleukin–6 (IL–6) Regulates Human Chorionic Gonadotropin Release through IL–6 Receptor on Human Trophoblasts," *Journal of Clinical Endocrinology and Metabolism* 71:436–441 (1990).
Hafler et al., "Mechanisms of Immune Memory: T Cell Activation and CD3 Phosphorylation Correlates with $Ta_1$ (CDw26) Expression," *The Journal of Immunology* 142:2590–2596 (1989).
Plebanski et al., "Primary and Secondary Human in vitro T–Cell Responses to Soluble Antigens are Mediated by Subsets Different CD45 Isoforms," *Immunology* 75:86–91 (1992).

*Primary Examiner*—Margaret Parr
*Assistant Examiner*—Phillip Gambel
*Attorney, Agent, or Firm*—Needle & Rosenberg, P.C.

[57] ABSTRACT

This invention provides an IL-6 dependent B-cell lymphoma cell line designated DS-1 deposited with the American Type Culture Collection, wherein the cell line is reactive with a monoclonal antibody produced by a hybridoma cell line designated 10D2F6 deposited with the American Type Culture Collection. The invention also provides a purified antigen reactive with a monoclonal antibody produced by 10D2F6. The antigen also exists on DS-1. Also provided is a method of detecting the presence of an antigen-stimulated T-cell comprising detecting the presence of the antigen on a lymphocyte. In addition, the invention provides a method of detecting the presence of a neoplastic cell comprising detecting the presence of the antigen on a cell which is not normal a T-cell.

4 Claims, No Drawings

MONOCLONAL ANTIBODY RECOGNIZING A SURFACE MOLECULE ON A SUBSET OF ANTIGEN-STIMULATED T CELLS AND ON CERTAIN MALIGNANCIES OF T AND B CELL ORIGIN

This application is a continuation of application Ser. No. 07/934,106, filed Aug. 21, 1992, now abandoned.

BACKGROUND OF THE INVENTION

Lymphocytes of B-cell lineage, with the proper cellular signals, ultimately mature into cells which secrete immunoglobulin molecules. Cell lines of B-cell lineage have been commonly produced by infecting cells with Epstein-Barr virus, but this technique produces cell lines at the B-cell stage of development which are not of tumor cell origin. While pre-B-cell lines such as REH and NALM-6 have been described, more mature B-cell lines which have not been Epstein-Barr virus-infected have been more difficult to obtain. Generally, most of the work on plasma cells has depended upon short-term culture of plasma cells from the bone marrow of patients with multiple myeloma. These cells live weeks to months in vitro.

While a number of tumor cell antigens have been described for epithelial cell tumors, few have been described for B-cell lineage malignancies. Many of these cells will express protein antigens on their surface during the active growth characteristic of malignant cells. In general, however, these antigens have proven to be upregulated receptors for cytokines (interleukin-2 and transferrin as examples) and not antigens unique to the tumor per se.

A cascade of events occurs which leads to the induction and maintenance of T- and B-lymphocyte activation. In general, these events are the result of the encounter, by T-cells, of a variety of stimuli. In vitro, stimuli which induce proliferation include mitogens, antibodies to specific T-cell receptors (such as to the T3 receptor) or reactivation of a subset of normal circulating lymphocytes by previously-encountered antigen (immunologic memory). With stimulation of these memory cells, a variety of surface proteins is expressed which participate in cellular activation and adhesion events. In general, these proteins are not unique to memory cells and can also be induced on the surface of nonmemory lymphocytes upon activation. The identification of a cell surface antigen which is uniquely associated with cells participating in the immunological memory response would be valuable for lymphocyte subpopulation manipulation in vitro and in vivo.

SUMMARY OF THE INVENTION

This invention provides an IL-6 dependent B-cell lymphoma cell line designated DS-1 deposited with the American Type Culture Collection, wherein the cell line is reactive with a monoclonal antibody produced by a hybridoma cell line designated 10D2F6 deposited with the American Type Culture Collection. The invention also provides a purified antigen reactive with a monoclonal antibody produced by 10D2F6. The antigen also exists on DS-1. Also provided is a method of detecting the presence of an antigen-stimulated T-cell comprising detecting the presence of the antigen on a lymphocyte. In addition, the invention provides a method of detecting the presence of a neoplastic cell comprising detecting the presence of the antigen on a cell which is not a normal T-cell.

DETAILED DESCRIPTION OF THE INVENTION

The invention provides an IL-6 dependent B-cell lymphoma cell line designated DS-1. The DS-1 cell line has a unique translocation t(8;22)(q24;q11) immediately 5' of the first myc exon and has high levels of myc expression. DS-1 has autologous expression of interleukin-6 mRNA and IL-6 protein production. The cellular morphology of DS-1 resembles a high grade B-cell lymphoma rather than a plasmacytoma or myeloma. While IL- 6 drives proliferation of DS-1 in a dose-dependent manner, it does not enhance immunoglobulin secretion. DS-1 is reactive with a monoclonal antibody produced by a hybridoma cell line designated 10D2F6. "10D2F6" can be used herein to identify both the hybridoma cell line and the antibody it produces.

Both DS-1 and 10D2F6 were deposited Aug. 21, 1992 pursuant to and in satisfaction of the Budapest Treaty for the deposit of microorganisms. The American Type Culture Collection is located at 12301 Parklawn Drive, Rockville, Md. 20852 USA. DS-1 has been assigned ATCC Accession No. CRL 11102. 10D2F6 has been assigned ATCC Accession No. HB 11103.

DS-1 has many unique features which can be used in various screening methods. For example, the cell line can be used to screen compounds for a cytotoxic effect on DS- 1. In such a method, the compound is simply added to the cell culture and the viability of the cells are noted. Those compounds having the greatest cytotoxic effect are then selected for use or for further clinical study. Likewise compounds can be screened for an inhibitory effect. An example of an inhibitory effect is the inhibition of IL-6 production by DS-1 or the effect of IL- 6 on DS-1 production. In yet another example, compounds can be screened to determine their effect on differentiation of DS-1. Any compound which promoted differentiation of DS-1 would be a candidate for an effective therapeutic to a neoplastic condition such as a B-cell lymphoma.

The invention also provides a purified antigen reactive with a monoclonal antibody produced by a hybridoma cell line designated 10D2F6. As used herein, "purified" means the antigen is sufficiently free of contaminants or cell components with which the antigen normally occurs to distinguish the antigen from the contaminants or cell components. Initially the antigen also exists on DS-1. This antigen is referred to herein as "the antigen" or "the 10D2F6 antigen."

The 10D2F6 antigen is not detected by flow cytometry on the surface of normal peripheral blood mononuclear cells, mitogen or alloantigen-stimulated B or T cells, but is induced on the cell surface of a subpopulation of CD3+ lymphocytes stimulated with antigen (e.g., influenza, tetanus, diphtheria). The 10D2F6 antigen is also detected on the surface of certain other malignant cell lines of T- and B-cell origin. Therefore, since the antigen occurs on cultured cells of various origins, it can be present on cells of various origins, including a broad range of neoplastic cells. One can routinely screen various cell lines for the antigen using the methods set forth in the Examples.

Evaluation of the cell binding characteristics of 10D2F6 using the Leukocyte Antigen Typing Database failed to identify a known CD classification. Preliminary radioimmunoprecipitation and sodium dodecyl sulfate/polyacrylamide gel electrophoresis (SDS/PAGE) studies indicated a protein of unusually large molecular size (approx. 300 kD) which was not reduced to smaller subunits using dithiothreitol or 2 mercaptoethanol on SDS/PAGE. DS-1 cells incubated with 10D2F6 and subsequently positively selected on magnetic beads covalent bound to suitable antibodies have significantly higher proliferation rates than the nonselected population of DS-1 cells. Thus, 10D2F6 antibody identified a new antigen present on the surface of certain malignant and specifically-activated normal lymphocytes. The absence of the 10D2F6 antigen on normal resting and mitogen-stimulated T-lymphocytes demonstrates that the antigen is associated with immunological memory.

Examples II through IV show that the antigen is uniquely expressed on T-cells proliferating following antigen stimulation. By "antigen stimulation" is meant a T-cell which (1) recognizes a peptide presented in the major histocompatibility complex and (2) is either actively proliferating or has become a memory cell. Thus, the invention provides a method of detecting the presence of an antigen-stimulated T-cell comprising detecting the presence of the antigen on a lymphocyte. Also provided is a method of ablating an antigen-stimulated T-cell comprising contacting a T-cell expressing the antigen with a cytotoxic moiety. The ablation can be used, for example, to immunosuppress a subject. In addition, the method can be used to treat an autoimmune disease, for example multiple sclerosis, by specifically targeting proliferating or memory T-cells. Such methods are detailed hereinbelow.

The Examples also show that the antigen, when expressed on cells other than normal T-cells, is a marker for a neoplastic cell. Therefore, the invention also provides a method of detecting the presence of a neoplastic cell comprising detecting the presence of the antigen on a cell which is not a T-cell (e.g. a B-cell lymphoma). Also provided is a method of ablating a neoplastic cell comprising contacting a neoplastic cell expressing the antigen with a cytotoxic moiety. Therefore, the method can be used to treat a neoplastic condition in a subject. Such methods are detailed hereinbelow.

As used herein, "antigen" when used in the detection or ablation context generally means detecting or ablating the antigen on an intact cell. However, for example in the neoplastic conditions, the antigen may exist independent of the cell and be detectable in a body fluid.

One example of the method of detecting the antigen is performed by contacting a fluid or tissue sample from the subject with an amount of a purified antibody specifically reactive with the antigen, cells containing the antigen, or fragments of the antigen, and detecting the reaction of the ligand with the antigen. As contemplated herein, the antibody includes any ligand which binds the antigen, for example, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus and the like.

The presence of the antigen can also be determined by detecting the presence of a nucleic acid specific for the antigen. The specificity of these sequences for the antigen can be determined by conducting a computerized comparison with known sequences, catalogued in GenBank, a computerized database, using the computer program Word Search or FASTA of the Genetics Computer Group (Madison, Wis.), which searches the catalogued nucleotide sequences for similarities to the gene in question.

Detecting the reaction of the ligand/antibody with the antigen can be facilitated by the use of a ligand that is bound to a detectable moiety by methods known in the art. Such a detectable moiety will allow visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-strepavidin (for light or electron microscopy) and alkaline phosphatase (for biochemical detection by color change). Likewise, cytotoxic moieties can be conjugated to the ligand/antibody by standard methods. Examples of cytotoxic moieties include ricin A chain, diptheria toxin and radioactive isotopes. The detection methods and moieties used can be selected, for example, from the list above or other suitable examples by the standard criteria applied to such selections (Harlow and Lane, Antibodies: A Laboratory Manual, Cold Spring Harbor Laboratory, Cold Spring Harbor, N.Y., 1988).

In the present invention, the step of detecting the reaction of the ligand with the antigen can be further aided, in appropriate instances, by the use of a secondary antibody or other ligand which is reactive, either specifically with a different epitope or nonspecifically with the ligand or reacted antibody.

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change.

A purified antibody specifically reactive with an immunoreactive epitope specific to the antigen is also provided. The term "reactive" means capable of binding or otherwise associating nonrandomly with an antigen. "Specific" immunoreactivity as used herein denotes an antigen or epitope (amino acid, protein, peptide or fragment) that does not cross react substantially with an antibody that is immunoreactive with other antigens. One such antibody described in the Examples is 10D2F6. Additional antibodies can be made by the procedure set forth in the Examples or by standard procedures (Harlow and Lane, Antibodies; A Laboratory Manual, Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen DNA clone libraries for cells secreting the antigen. Those positive clones can then be sequenced as described in the Examples or by other methods, see, for example, Kelly et al., Bio/Technology 10:163-167 (1992) and Bebbington et al., Bio/Technology 10:169-175 (1992).

The present invention further provides a kit for detecting the antigen. Particularly, the kit can detect the presence of an antigen specifically reactive with the antibody or an immunoreactive fragment thereof. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Once the nucleotide sequence of the antigen is determined, the diagnostic kit of the present invention can alternatively be constructed to detect nucleotide sequences specific for the antigen comprising the standard kit components such as the substrate and reagents for the detection of nucleic acids. Because neoplastic cells and antigen-stimulated cells can be diagnosed by detecting nucleic acids specific for the antigen in tissue and body fluids such as urine, saliva and serum, it will be apparent to an artisan that a kit can be constructed that utilizes the nucleic acid detection methods, such as specific nucleic acid probes, primers or restriction fragment length polymorphs in analyses. It is contemplated that the diagnostic kits will further comprise a positive and negative control test.

The particular reagents and other components included in the diagnostic kits of the present invention can be selected from those available in the art in accord with the specific diagnostic method practiced in the kit. Such kits can be used to detect the antigen in tissue and fluid samples from a subject.

An isolated immunogenically specific epitope or fragment of the antigen is also provided. A specific immunogenic epitope of the antigen can be isolated from the whole antigen by chemical or mechanical disruption of the molecule. The purified fragments thus obtained can be tested to determine their immunogenicity and specificity by the methods taught herein. Immunoreactive epitopes of the antigen can also be synthesized directly. An immunoreactive fragment is defined as an amino acid sequence of at least about 5 consecutive amino acids derived from the antigen amino acid sequence.

By the discovery of the antigen, the invention also provides the nucleotide sequence encoding the antigen. The sequence encoding antigen can be determined by standard procedures. For example, the amino terminal sequence of the antigen can be determined and a corresponding nucleotide sequence can be deduced. This nucleotide sequence can then be used to make a probe to hybridize sequences from a gene library.

The selection of a nucleic acid that encodes the antigen or a specific immunoreactive epitope can be accomplished by screening clone libraries with the probe for the antigen (see also, Sambrook et al. Molecular Cloning: A Laboratory Manual, 2nd ed. Cold Spring Harbor, N.Y., 1989). The recombinant plaques or colonies can also be screened for antigen production via immunoblot, and enzyme immunoassays. Antigen expressing clones can then be subcloned.

Factors that are involved in successful expression of a cloned gene in a particular system include, solubility within the cell, non-toxicity to the cell, possible secretion by the expressing cell, low levels of proteolytic digestion by the cell and ease of purification in the system. Folding, disulfide bond formation, as well as post-translational modifications (glycosylation, phosphorylation, etc.) can affect expression and synthesis of proteins; these factors differ according to the host cells used for expression.

In addition to the above described vector there are numerous E. coli expression vectors known to one of ordinary skill in the art useful for the expression of the antigen. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems.

The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either Gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted DNAs in mammalian cells (such as COS7).

For the above expression system, antibodies generated to the antigen, such as 10D2F6, can be used to follow and to quantitate the antigen produced; the antibodies are particularly useful for following the purification of the antigen as, for example, in an E. coli system.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The antigen of this invention can be used in the construction of a vaccine comprising an immunogenic amount of the antigen and a pharmaceutically acceptable carrier. The vaccine can be the entire antigen, the antigen on a cell surface, or an epitope specific to the antigen or it can be potentially cross reactive with antibodies to other neoplastic antigens. The vaccine can then be used in a method of preventing the neoplasm. Alternatively, the antigen can be used to ablate antigen-stimulated T-cells for immune suppression or treatment of an autoimmune disease, such as multiple sclerosis, in a subject by administering the vaccine to the subject. Furthermore, the fact that other disease syndromes are associated with the antigen, means that such diseases can also be prevented by use of the vaccines of this invention.

Immunogenic amounts of the antigen can be determined using standard procedures. Briefly, various concentrations of a putative specific immunoreactive epitope are prepared, administered to an animal and the immunological response (i.e., the production of antibodies) of an animal to each concentration is determined.

The pharmaceutically acceptable carrier in the vaccine of the instant invention can comprise saline or other suitable carriers (Arnon, R. (Ed.) Synthetic Vaccines I:83–92, CRC Press, Inc., Boca Raton, Fla. 1987). An adjuvant can also be a part of the carrier of the vaccine, in which case it can be selected by standard criteria based on the antigen used, the mode of administration and the subject (Arnon, R. (Ed.) Synthetic Vaccines I:93–103, CRC Press, Inc., Boca Raton, Fla., 1987). Methods of administration can be by oral or sublingual means, or by injection, depending on the particular vaccine used and the subject to whom it is administered.

EXAMPLE I

Characterization of the DS-1 Cell Line

The DS-1 cell line was derived from an immunodeficient patient with intestinal lymphangiectasia and lymphoma by culturing malignant pleural effusion cells with interleukin-6 (IL-6) in vitro. In brief, DS-1 is an autocrine-producing and IL-6-dependent cell line of B-cell lineage which resembles lymphoid malignancies arising in patients with AIDS and other immunodeficiency disorders. The cell line has been successfully established in stable long-term culture in vitro and may be useful for developing strategies for diagnosis and treatment of B-cell lymphomas in immunocompromised patients.

MATERIALS AND METHODS

Cell Culture. DS-1 cells were obtained for culture from pleural effusion aspirates. DS-1 cells were isolated by density centrifugation over a sodium diatrizoate/Ficoll gradient (LSM, Organon Teknika Corp., Durham, N.C.). Standard culture medium was RPMI 1640 (GIBCO, Grand Island, N.Y.) which was supplemented to 10% FCS, 2 mM L-glutamine 100 U/mL penicillin G and 100 mg/mL streptomycin sulfate (akk GIBSO). Long-term culture was achieved at a cell density of $1-3\times10^5$ cells/mL using recombinant IL-6, 10U/mL. Where specified, "minimal medium" was RPMI 1640 containing penicillin and streptomycin as described above, 2.5 mg/mL transferrin and 0.1% bovine serum albumin, fraction V (Sigma Chemical Co., St. Louis, Mo.).

Cytokines and antibodies. All cytokine preparations were recombinant human products. IL-6 was purchased from Genzyme Corp. (Boston, Mass.), IL-2, IL-3, IL-4 and IL-7 from Upstate Biotechnology Inc. (Lake Placid, N.Y.) and IL-lb a kind gift of Dr. G. Tosado, CBER, FDA, Bethesda, MD. Both rabbit polyclonal anti-human IL-6 and anti-IL-2 antibodies were purchased from Genzyme Corp.,Boston, Mass. Mouse monoclonal anti-IL-6 MH166 (Matsuda et al., *Eur. J. Immunol.* 18:951–956 (1988)) and anti-IL-6 receptor PM-1 (Hirata et al., *J. Immunol.* 143:2900–2906 (1989)) antibodies were the kind gifts of Prof. T. Kishimoto, Osaka, Japan.

Electron Microscopy. Cells were washed with PBS and subsequently fixed in 2.5% glutaraldehyde in PBS (pH 7.4) at room temperature for 2 h, postfixed in $OsO_4$, and embedded in Maraglas 655 (Ladd Research Industries, Burlington, Vt.). Sections were stained with uranyl acetate-lead citrate and examined in a Phillips 201 electron microscope.

Cell Line Immunophenotyping. DS-1 cells were studied with the following monoclonal antibodies: CD19 (Leu12), CD20 (Leu16), CD7 (Leu9 and 3A1), CD14 (LeuM3), CD45 (HLE), CD38 (T10), PCA-1 (plasma cell antigen), anti-kappa, anti-lambda and PM-1. The Leu-series reagents and anti-light chain reagents were obtained from Becton Dickinson Immunocytometry Systems (San Jose, Calif.) and the remainder of the reagents were from Coulter Immunology (Hialeah, Fla.). One million cells were stained with the manufacturer's recommended volume of directly conjugated or unconjugated antibody for 30 m at 4° C. The cells were then washed with PBS and analyzed or the unconjugated reagents were counter-stained with goat $Fab'_2$ anti-mouse IgG conjugated to FITC (Caltag, San Francisco, Calif.) followed by washing and analysis using a FACScan (Becton Dickinson) flow cytometer. Viability of the cells was assessed by trypan blue exclusion. Cells were gated based on forward and side light scatter to exclude debris. The percent of positive cells for each reagent was determined based upon irrelevant murine controls of the appropriate IgG subclass.

Proliferation assays. DS-1 cells were centrifuged at 200×g for 8 m, washed and recentrifuged 3 times in minimal culture medium containing no supplemental IL-6, and resuspended in minimal medium so that the final concentration was $9\times10^4$ cells/mL. The cells were cultured for 48 h in quadruplicate in 96-well, flat-bottomed microtiter plates (Costar, Cambridge, Mass.) in a final volume of 200 mL. All cytokine and antibody reagents were prepared in minimal medium at desired concentrations. One mCi of [$^3$H]TdR (6.7 Ci/mM, New England Nuclear, Boston, Mass.) in 50 mL RPMI 1640 was added to each culture well during the last 16 h of culture, the cells were harvested onto filter paper and

[³H]TdR incorporation counted by liquid scintillation spectroscopy (LS-3801, Beckman Instruments, Inc., Fullerton, Calif.). Interassay proliferations were compared by calculation of stimulation indices using the appropriate mean control values.

IL-6 Receptor Binding. DS-1 cells were washed three times in HBSS (GIBCO) and resuspended at $2 \times 10^6$ cells/50 mL in ice-cold binding buffer (RPMI 1640 containing 10% FCS, glutamine, penicillin and streptomycin as above and 0.01% sodium azide [Sigma]). To each tube of $2 \times 10^6$ cells, 25 mL of serially diluted 6 mM unlabeled IL-6 or buffer alone was added and incubated at 4° C. for 1 hour. Thereafter, [$^{125}$I]IL-6 (Amersham Corp., Arlington Heights, Ill.; specific activity 1000Ci/mM) was diluted in binding buffer to 20 nM and 25 mL serial dilutions added to each tube of cells in the presence or absence of unlabeled IL-6. The cells were incubated at 4° C. for 2 h and subsequently microcentrifuged over oil for 2 m. The bottom of the tube was cut to obtain the cell pellet and both bound and free cpm were measured in a Beckman gamma 4000. Total receptors/cell and receptor association constants were determined by the method of Scatchard (D. Scatchard, *Ann. N.Y. Acad. Sci.* 51:660–672 (1949)).

IgG ELISA. DS-1 cells, 10 mL ($3 \times 10^5$ cells/mL) were incubated in minimal medium in the presence or absence of IL-6 for 72 h. Cell-free culture supernatants were obtained by centrifugation at 200×g for 8 m at 4° C. Saturated ammonium sulfate was added to supernatant at a final concentration of 45% v/v, incubated at room temperature for 2 h and microcentrifuged. Precipitates were resuspended in PBS to the original volume and dialyzed into PBS overnight at 4° C. with frequent buffer changes.

Cell pellets were washed with PBS and resuspended at room temperature for 1 h in PBS containing 1% Triton X-100 (RPI, Elk Grove Village, Ill.). Cell lysates were microcentrifuged for 5 m, the supernatants carefully removed and dialyzed against PBS overnight with frequent buffer changes. Following this, flat-bottomed 96-well microtiter plates (Costar) were precoated overnight in a humidified container at 4° C. with goat anti-human polyvalent immunoglobulin antiserum (Sigma), diluted 1:2000 in carbonate buffer pH 9.0. Microtiter wells were washed thrice with PBS/Tween 20; 100 mL of lysates and supernatants serially diluted in PBS were added to each well and incubated at RT for 2 h. Following repeat washings, alkaline phosphatase-conjugated goat anti-human IgG, gamma-chain specific (Sigma), was diluted 1:1000 in PBS and 100 mL added to each well and incubated for 1 h. Wells were again washed and 100 mL of r-nitrophenyl phosphate, 1 mg/mL in diethanolamine buffer, was added to each well. Optical densities were measured in a BioRad EIA 2550 microplate reader at 405 nM and IgG concentrations determined by an internal standard curve constructed from serially diluted human IgG (Gamimune N, Cutter Biological, Elkhart, Ind.) in each plate. Assays for interleukin-6. Cells were cultured in minimal medium at a density of $1 \times 10^6$ cells/mL for 24 and 48 h. Cell-free culture supernatant was obtained after centrifugation at 200×g for 10 m. The presence of IL-6 in culture supernatants was assayed using the IL-6-dependent B9 murine hybridoma proliferation assay (Aarden et al. *Eur. J. Immunol.* 17:1411–1416 (1987)) (kindly performed by Dr. G. Tosado), with a lower limit of sensitivity of 5 pg/mL. In addition, culture supernatants were assayed using a human IL-6 ELISA (Genzyme Corp.). Northern blot analysis for IL-6. Total cellular RNA was isolated using guanidinium thiocyanate/phenol extraction (RNAzol B, Cinna/Biotecx Laboratories International, Inc., Friendswood, Tex.) (Chomczynski and Sacchi, *Anal. Biochem.* 162:156–159 (1987)). PolyA$^+$ mRNA-enriched samples were prepared by isolation on oligo(dT) cellulose (Fast Track mRNA Isolation Kit, Invitrogen Corp., San Diego Calif.) using the manufacturer's recommended protocol. In either case, RNA purification was followed by electrophoresis of 20 µg of RNA in 1% agarose/formaldehyde gels. PHA (GIBCO)-stimulated normal peripheral blood mononuclear cell total RNA, isolated as described above, served as the positive control.

RNA was transferred overnight onto nitrocellulose membranes (BAS NC, Schleicher & Schuel, Keene, N.H.), subsequently hybridized with the IL-6 DNA probe pCSF309 (ATCC, Rockville, Md. #67153), which had been labeled with [$^{32}$P] by the random primer extension method, and evaluated by autoradiography. In some cases, the nitrocellulose membranes were stripped of IL-6 probe in boiling water and rehybridized with a [$^{32}$P]-labeled probe for β-actin. Semiquantitation of mRNA was accomplished by the measurement of signal intensity of the IL-6 probe adjusted for b-actin intensity by image analysis on a Phosphor Imager (Molecular Dynamics, Sunnyvale Calif.). Culture conditions and response to IL-6 and other cytokines. The tumor cells were initially cultured under various conditions with the addition of cytokines which might augment the proliferation of a B-cell-derived cell line in vitro. The initially isolated tumor grew poorly in various fetal calf serum (FCS)-containing medium formulations, including supplementation with IL-2. By contrast, excellent proliferation and cell viability was noted with the addition of IL-6 to medium containing 10% FCS. The addition of FCS alone to medium caused modestly increased spontaneous proliferation over baseline values as measured by [³H]TdR. However, this occurred without increases of cell numbers in culture.

Under standard medium conditions, the magnitude of the proliferative response of the cell line was IL-6 dose-dependent, with significant increases over baseline values occurring at 1 U/mL and maximal rates occurring typically between 100 and 1000 U/mL. This proliferative response to IL-6 was accompanied by increases of cell numbers. When $0.9 \times 10^2$ cells were cultured in the presence of 10U/mL IL-6, there was approximately a five-fold increase of cell number by day 4 of culture. As noted above, no net increase of cell number was noted in those cells cultured in the absence of exogenous IL-6 and the overall percent viability was poor. No significant change of DS-1 proliferation, as measured by [³H]TdR incorporation, was noted with IL-1b, IL-2, IL-3, IL-4, or IL-7. The possible synergistic effects of IL-2, IL-3 or IL-4 with IL-6 were also investigated. Proliferation rates using the combinations of IL-2/IL-6, IL-3/IL-6 and IL-4/IL-6 were no different than IL-6 alone.

The magnitude of spontaneous and IL-6 driven [³H]TdR incorporation at 48 h was considerably diminished by the addition of polyclonal or monoclonal anti-IL-6 to the culture medium (Table 1). Interestingly, the degree of diminution of proliferation was greater in the cultures receiving supplemental IL-6 compared to those receiving none (Table 1). Monoclonal anti-IL-6 receptor (IL-6R) antibody decreased proliferation to a similar degree as monoclonal anti-IL-6, whether in the presence or absence of exogenous IL-6. However, the simultaneous addition of both antibodies caused no additive inhibition.

TABLE 1

|  | Medium | Medium + IL-6 |
|---|---|---|
| No additive | 3559 ± 553 | 25883 ± 1015 |
| Polyclonal aIL-6 | 2597 ± 174 (37%) | 11419 ± 592 (56%) |
| Monoclonal aIL-6 | 1627 ± 196 (54%) | 1984 ± 1004 (92%) |
| Monoclonal aIL-6R | 1664 ± 239 (53%) | 2493 ± 380 (90%) |

Summary of data from one of three experiments with similar results. Numbers are CPM [$^3$H]TdR in DS-1 cells with percent inhibition in parentheses. Medium = RPMI 1640 containing 10% FCS (see text). Supplemental IL-6 was 10 U/mL medium. Control studies were performed with the addition of a polyclonal rabbit anti-IL-2 antibody, prepared in a similar manner to the polyclonal anti-IL-6 antibody. These showed no effect on proliferation of DS-1.

Morphologic and phenotypic cell characteristics. Microscopic assessments of the cell line were performed in order to characterize the probable cell lineage. By electron microscopy, the cells lacked attachments, exhibited irregular surfaces and contained some rough endoplasmic reticulum, but not to the extent usually observed in plasma cells. The nuclei were indented and the typical cartwheel arrangement of the heterochromatin associated with plasma cells was not observed. Similarly, Russell bodies were absent. These ultrastructural features are most compatible with those associated with lymphocytes of B-cell origin.

Immunophenotypic evaluation of DS-1 demonstrated the presence of some B-cell surface antigens (Table 2). While the cells showed no detectable pan-leukocyte antigen, CD45, nor the pan B-cell antigens CD19 or CD20, they demonstrated the presence of HLA Class II antigen and were essentially 100% positive for PCA-1. In addition, kappa light chain was present on the cell surface of 22 % of the cells. These findings were similar to the initial phenotype profile of the tumor, although the original tumor cells also expressed low levels of 3A-1 antigen. Antigens typically associated with T cell lineage were absent from the cell line (Table 2). Finally, at least 35% of the cell population demonstrated detectable surface IL-6 receptors by flow cytometry using the monoclonal antibody PM1.

TABLE 2

| Antigen | % Positive | Antigen | % Positive |
|---|---|---|---|
| CD 19 | NR | CD2 | <5 |
| CD 20 | NR | CD3 | <5 |
| CD 38 | NR | CD4 | NR |
| CD 45 | NR | CD5 | NR |
| PCA | 99 | CD7 | NR |
| HLA Class II | 38 | CD8 | NR |
| Ig kappa | 22 | CD30 | NR |
| Ig lambda | NR | HLA Class I | 100 |
| IL-6 receptor | 35 | | |

NR = nonreactive

IL-6 binding to DS-1. Since antibody to the IL-6R was found to inhibit DS-1 cell proliferation, and FACS analysis demonstrated that IL-6R antibody binds to the cell surface, specific binding studies were performed to further evaluate the number and nature of the IL-6 receptors. The results of the [$^{125}$I] IL-6 binding studies indicate the presence of both low and high affinity IL-6 receptors. The $K_d$ and number of binding sites/cell were $1.2 \times 10^{-11}$ M and 590, respectively, for the high affinity receptors and $6.7 \times 10^{-10}$ and 3970 for the low affinity receptors.

Detection of IL-6 product and mRNA. Because DS-1 cells demonstrated both spontaneous and IL-6 driven proliferation, studies were performed to determine whether the cell line constitutively produced IL-6. Neither the B9 IL-6 bioassay nor the IL-6 ELISA were capable of detecting IL-6 protein in cell culture supernatants, using short term cell culture densities as high as $1.0 \times 10^6$ cells/mL. Likewise, no DS-1 mRNA for IL-6 was identified in whole RNA samples by northern analysis using the pCSF309 probe for IL-6, although IL-6 message was readily identified in total RNA isolates from PHA-stimulated normal peripheral blood mononuclear cells. By contrast, IL-6 message was detected in polyA$^+$ selected mRNA from DS-1 cells, whether cultured in the presence or absence of exogenous IL-6. When the image intensities of IL-6 mRNA under these two conditions were adjusted for the relative intensity of β-actin signal, the values for IL-6 mRNA in the absence and presence of IL-6 were virtually identical.

Immunoglobulin production. Due to the fact that IL-6 enhances immunoglobulin synthesis in stimulated normal B-cells, studies of IL-6-induced immunoglobulin synthesis in DS-1 were performed. Cell lysates from DS-1 cultured in the absence of exogenous IL-6 contained 872±300 ng IgG/ $10^6$ cultured cells compared to 948±236 ng/$10^6$ cells for those cultured with IL-6, 10U/mL. Contrary to the proliferation data, no significant difference of supernatant IgG production was found in unstimulated cells (1050±314 ng/mL) compared to IL-6 stimulated cells (830±310 ng/mL).

EXAMPLE II

Production of Hybridoma 10D2F6

Methods

BALB/c mice were introperitoneally immunized with viable DS-1 cells ($5 \times 10^6$ cells in 0.5 mL PBS) at two week intervals on three occasions followed by a final intravenous injection. Three days following the last injection, spleens were sterilely removed from 5 mice and pooled, minced, and sieved through wire mesh to produce a single cell suspension. Hybridomas were produced by fusing $1 \times 10^8$ splenocytes with $1 \times 10^7$ Sp2/0 mouse myeloma cells, which had previously been grown in 8-azaguanine. Standard polyethylene glycol cell fusion techniques were employed (*Current Protocols in Immunology*, Coligan et al. eds., John Wiley & Sons, New York, pp. 2.5.4–2.5.7 (1992)). Cells were cultured at 37° C. in a humidified $CO_2$ incubator. Screening occurred when cell growth reached 50% confluence.

Screening of hybridomas for antibodies-of-interest was accomplished by performing proliferation and cytotoxicity assays using hybridoma supernatant and DS-1 cells. For the proliferation assay DS-1 cells were growing in log phase in RPMI 1640 medium supplemented with FCS 10%, recombinant IL-6 10U/mL (Genzyme, Cambridge Mass.) and L-glutamine, penicillin and streptomycin. Cells were centrifuged at 200×g, washed twice with fresh medium and resuspended at $1.4 \times 10^5$ cells/mL in medium containing no IL-6. 100 ul of the cell suspension were added to wells in 96-well sterile microtiter plates. 50 ul of the cell-free supernatant from the hybridoma well to be tested were added to the DS-1 cells. 50 ul HAT/DMEM medium served as negative controls. Cells were incubated at 37° C. in a humidified $CO_2$ incubator for 32 hours at which time 1 uCi of $^3H[TdR]$ was added to each well. Cells were harvested onto filter mats at 48 hours and relative proliferation rates determined by the amount of $^3H[TdR]$ incorporation as measured by scintillation spectroscopy.

For the cytotoxicity assay, $5 \times 10^6$ DS-1 cells were washed as described above and then incubated with 200 uCi fresh $^{51}[Cr]$ at 37° C. for 90 minutes with frequent gentle resuspension. Cells were then washed in RPMI medium twice and adjusted to a concentration of $1 \times 10^5$ cells/mL. 100 ul of the cell suspension was incubated with 50 ul hybridoma supernatant and 50 ul 3 to 4 week newborn rabbit complement in round-bottom microtiter plates for 1 hour. Plates were then centrifuged at 200×g for 10 minutes. Supernatants were separated from pellets using a Titertek supernatant harvesting system, radioactivity measured in a gamma counter and the percent $^{51}[Cr]$ release calculated. Release was compared to negative control (medium alone) and maximum release determined by cells lysed using 1:20 Triton-X100 in $H_2O$.

Results

A total of 720 hybridoma wells were initially cultured. In the presence of supernatant from hybridoma well 10D2, DS-1 cells had a mean proliferation rate on the initial screens which was <−2 SD of the mean control value. The cells in well 10D2 were then cloned by limiting dilution. The mean proliferation ($^3H[TdR]$ incorporation) of DS-1 in the presence of supernatant from clone 10D2F6 was 2,093 dpm compared to the control mean of 5,449±609 dpm(−3SD=3, 622). The initial hybridoma supernatant from 10D2 demonstrated only a modest increase of $^{51}[Cr]$ release in the cytotoxicity assay with a value of 231 dpm (control=106±12 dpm, maximum release=672 dpm).

EXAMPLE III

Purification and Characterization of 10D2F6 Monoclonal Antibody

Methods

The immunoglobulin isotype from 10D2F6 hybridoma supernatant was determined using isotype-specific immunodiffusion. For monoclonal antibody production, BALB/c mice were primed with pristane, 0.5 mL intraperitoneally. After 10 days to 2 weeks, $5 \times 10^6$ 10D2F6 hybridoma cells in 0.5 mL PBS were injected IP. Ascites was harvested by paracentesis and purified by staphylococcus protein A affinity chromatography (BioRad).

For DS-1 proliferation assays using 10D2F6 ascites, DS-1 cells were grown in RPMI 1640 containing 10% FCS and 10U/mL IL-6. 100 µl of washed DS-1 cells, $1.8 \times 10^5$/mL, with or without IL-6 were cultured in triplicate with 100 µl of monoclonal antibody ascites serially diluted in culture medium. $^3H[TdR]$ incorporation was performed as described above.

Competitive binding experiments of 10D2F6 antibody with $^{125}I[IL-6]$ were performed on DS-1 cells. Briefly, dilutions of 10D2F6 antibody were added to DS-1 cells in the presence of radiolabeled IL-6 and binding inhibition determined. Buffer alone and the anti-IL-6 monoclonal antibody PM-1 (gift of Dr. T. Kishimoto) served as negative and positive controls respectively.

The flow cytometry characteristics of 10D2F6 antibody, as well as PM-1 antibody were compared on DS-1 cells. Briefly, 1 ug of unlabeled monoclonal antibody was incubated with $1 \times 10^6$ DS-1 cells, followed by FITC-conjugated goat anti mouse antibody. The $IgG_1$ murine monoclonal antibody MOPC21 served as a negative control.

Results

Monoclonal antibody 10D2F6 is an $IgG_1$ isotype by radial immunodiffusion. In early experiments with purified culture supernatant and ascites, the antibody demonstrated 30–50 percent inhibition of DS-1 proliferation over control values in the absence of IL-6; there was no significant inhibition in the presence of IL- 6. Similar experiments performed somewhat later with the same antibody preparations showed that the DS-1 cell line had become refractory to the inhibitory effects of 10D2F6 antibody. However, the 10D2F6 surface phenotype by flow cytometry remained unchanged.

Competitive binding studies showed that while anti-IL-6 receptor antibody PM-1 almost completely abrogated IL-6 binding to DS-1, no inhibition was seen with 10D2F6. In addition, the flow cytometry histograms for IL-6 receptor antibody and 10D2F6 are distinctly different: approximately 35% of DS-1 demonstrate low positive IL-6 receptor antibody staining while 90% of DS-1 had surface 10D2F6 staining in a strongly positive bimodal pattern.

EXAMPLE IV

Distribution and Characterization of the 10D2F6 Antigen

Methods

The presence of the surface ligand for 10D2F6 on a number of hematopoietic cell lines and normal peripheral blood mononuclear cells (PBMC) was investigated by flow cytometry using conditions as described above. In addition, the coexpression of the antigen on resting and stimulated PBMC with antibodies to known surface markers was evaluated using dual fluorescence cell labeling. These markers included CD3, CD4, CD8, CD13, CD16, CD20, CD28, CD45RA, CD45RO and Ta1.

For the stimulated PBMC studies, mononuclear cells were purified on a Ficoll density gradient. Pokeweed mitogen-stimulated cells were evaluated on days 7 and 14; OKT3, phytohemagglutinin, tetanus, diphtheria and influenza-stimulated cells on days 3, 4 and 6. Alloantigen-stimulated mononuclear cells were generated using $1 \times 10^6$ stimulator and responder cells/mL. Stimulators were irradiated with 1500 rads and cells were cultured for 6 days prior to flow cytometric analysis. The degree of proliferative response at the time of flow cytometry study was assessed by $^3H[TdR]$ incorporation and, in some cases, CD25 cell surface expression.

Radioimmunoprecipitation studies of the 10D2F6 antigen have been performed using DS-1 cells. Briefly, 1×10$^8$ DS-1 cells were biosynthetically labeled by culturing for 4 hr with $^{35}$S[methionine] in methionine-free RPMI 1640 containing 10% dialyzed FCS, followed by cell washing and subsequent lysis by buffer containing 1% Triton X-100, and protease inhibitors. Cell lysates were precleared and ultimately immunoprecipitated using Pansorbin cells plus a polyclonal rabbit anti-mouse IgG$_1$ antibody. SDS/PAGE was performed in 4%–12% gradient and 5% gels in the presence or absence of 2-ME or DTT in the sample buffer. The negative control for the immunoprecipitation was a murine IgG$_1$ monoclonal anti-human endothelial antibody, 14E5, which demonstrates no evidence of DS-1 binding by flow cytometry. Positive control for the immunoprecipitation was an anti-HLA class I antibody.

Immunomagnetic separation of DS-1 and U266 cells was performed using magnetic beads covalently bound to goat anti-mouse IgG in order to determine (1) the stability of the 10D2F6 phenotype on growing cells and (2) to determine whether 10D2F6 positive and negative cells proliferate at different rates as determined by $^3$H[TdR] incorporation. Briefly, cells were separated on beads following a 30 min incubation with 10D2F6 at 4° C. Sorted cells underwent flow cytometric analysis for 10D2F6 binding and also had $^3$H[TdR]studies performed as described above. Some of the sorted cells were placed back in culture flasks and cultured under standard conditions for an additional 72 hours, following which flow cytometric analysis was repeated.

Results

The 10D2F6 antigen is not exclusively expressed on the surface of DS-1 cells, since it was detected on several other cell lines tested, including an IL-2-dependent T cell line from a patient with Adult T-Cell Leukemia and a small percentage of the myeloma cell line, U266 (Table 3). In addition, the Table shows that there was no significant 10D2F6 antigen on the surface of normal, resting PBMC.

TABLE 3

Cell Line and PBMC 10D2F6 Antigen by Flow Cytometry

|  | Identification | % Positive |
|---|---|---|
| Cell Lines | IL-2 dependent T cell | 100 |
|  | DS-1 | 91 (bimodal) |
|  | U266 | 21 |
|  | HUT102 | 10 |
|  | K562 | 6 |
|  | Jurkat | <3 |
|  | MOLT4 | Neg |
|  | EBV-B-cell | <3 |
| Normal PMBC | Monocytes | <3 |
|  | Lymphocytes | Neg |
|  | Granulocytes | Neg |

Following mitogen and alloantigen stimulation, there was no significant expression of 10D2F6 antigen on the surface of PBMC (Table 4). When PBMC are stimulated with specific antigen, however, the ligand is induced, reaching maximal expression on a subpopulation of antigenstimulated cells by day 6 of culture (Table 4). Lymphocyte subset evaluation studies demonstrated that 10D2F6 binding was confined to T cells. It was distributed between CD4+ and CD8+ T cells (approximately and 40% respectively) and is also coexpressed on subsets of CD45RA, CD45RO and Tal positive cells. There was a significant correlation of the percent of antigenstimulated cells expressing 10D2F6 ligand and the 3H[TdR] incorporation (R=0.838, p=0.005), suggesting the association of 10D2F6 ligand expression and the specific proliferative recall response to antigen. Analysis of the 10D2F6 cell binding data using the Leukocyte Antigen Typing Database has failed to identify a CD-classified candidate for the 10D2F6 target molecule.

TABLE 4

Expression of 10D2F6 Antigen on Activated PBMC

|  | Stimulant | % Positive |
|---|---|---|
| Mitogen | Phytohemagglutinin | <3 |
|  | Pokeweed-7 day | Neg |
|  | Pokeweed-14 day | Neg |
|  | OKT-3 | <3 |
| mLR |  | Neg |
| Antigen | Tetanus | 12 |
|  | Diphtheria | 7 |
|  | Influenza | 5 |

Preliminary evaluation of the cell surface ligand for D2F6 from DS-1 cell lysates demonstrated a molecular moiety of an unusually large molecular size, approximately 300 kD, which was not reduced into constituent subunits with 2-ME or DTT.

Initial studies of cells separated by 10D2F6 binding to immunomagnetic beads have been performed using DS-1 and U266 cells. The results, seen in Table 5, indicate that positively selected cells have significantly greater proliferative rates than those cells remaining as reflected by $^3$H[TdR] incorporation. The degree of difference of proliferative rates was reflected in the difference of 10D2F6 binding in the respective positive and nonselected (remaining) populations. Further studies are ongoing to determine the actual differences between positive and negative selected populations in these cell lines and in antigen-stimulated PBMC.

TABLE 5

| | Studies of Immunomagnetic Separation of DS-1 and U266 | | | |
|---|---|---|---|---|
| | DS-1 | | U266 | |
| | % 10D2F6+ | $^3$H[TdR] (cpm) | % 10D2F6+ | $^3$H[TdR] (cpm) |
| + Selected | 86.4 | 11,361 ± 615 | 40.8 | 7,965 ± 475 |
| Nonselected | 74.3 | 7,565 ± 1390 | 23.1 | 3,475 ± 431 |

Throughout this application various publications are referenced. The disclosures of these publications in their entireties are hereby incorporated by reference into this application in order to more fully describe the state of the art to which this invention pertains.

The preceding examples are intended to illustrate but not limit the invention. While they are typical of examples that might be used, other procedures known to those skilled in the art may be alternatively employed.

What is claimed is:

1. A purified antibody which specifically binds the same antigen as the monoclonal antibody produced by the hybridoma cell line designated 10D2F6 having ATCC Accession No. HB 11103, wherein the purified antibody binds an antigen which exists on an IL-6 dependent B-cell lymphoma cell line designated DS-1 having ATCC Accession No. CRL 11102 wherein the purified antibody also specifically binds an antigen on antigen-stimulated T cells, but not on non-stimulated T cells.

2. The antibody of claim 1, labeled with a detectable moiety.

3. The antibody of claim 1, bound to a solid support.

4. The antibody of claim 1, conjugated to a cytotoxic moiety.

* * * * *